United States Patent
Okino et al.

(10) Patent No.: US 8,652,821 B2
(45) Date of Patent: Feb. 18, 2014

(54) STABILIZED PROTEASE-CONTAINING SOLUTIONS FOR PURIFYING RNA-FREE DNA

(75) Inventors: Steven T. Okino, San Carlos, CA (US); Yan Wang, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 7 days.

(21) Appl. No.: 13/276,553

(22) Filed: Oct. 19, 2011

(65) Prior Publication Data

US 2012/0100597 A1 Apr. 26, 2012

Related U.S. Application Data

(60) Provisional application No. 61/405,107, filed on Oct. 20, 2010.

(51) Int. Cl.
*C12N 9/22* (2006.01)

(52) U.S. Cl.
USPC .......................................................... 435/199

(58) Field of Classification Search
None
See application file for complete search history.

(56) References Cited

U.S. PATENT DOCUMENTS

| 5,128,247 | A | 7/1992 | Koller |
| 2002/0177139 | A1 | 11/2002 | Greenfield et al. |
| 2009/0130237 | A1 * | 5/2009 | Cohen .......................... 424/741 |
| 2009/0286304 | A1 | 11/2009 | Latham et al. |

FOREIGN PATENT DOCUMENTS

| JP | 2002-209588 A * | 7/2002 |
| WO | WO 00/29618 A1 | 5/2000 |
| WO | WO 2012/054613 A2 | 4/2012 |

OTHER PUBLICATIONS

Micard et al., "Purification of RNA-free plasmid DNA using alkaline extraction followed by Ultrogel A2 column chromatography", Anal Biochem. Jul. 1985;148(1): Abstract.*
Meijer et al., "Use of Mitochondrial DNA as a Sensitive and Specific Marker for Localization of Mitochondria in Fractionated Plant Extracts", Plant Molecular Biology Reporter, 1996, 14(4):353-362.*
Loading Buffer Recipe from Matt Lewis—Methodbook.net <http://www.methodbook.net/dna/agarogel.html#loadingbuff>—copyright 2001; last visisted Mar. 28, 2013.*
Arnold, Ulrich et al., "Thermal unfolding and proteolytic susceptibility of ribonuclease A," Eur. J. Biochem., vol. 237, pp. 862-869 (1996).

* cited by examiner

*Primary Examiner* — Suzanne M Noakes
(74) *Attorney, Agent, or Firm* — Kilpatrick Townsend & Stockton LLP

(57) ABSTRACT

The present invention provides compositions and methods for purifying RNA-free DNA from a sample.

22 Claims, No Drawings

STABILIZED PROTEASE-CONTAINING SOLUTIONS FOR PURIFYING RNA-FREE DNA

CROSS-REFERENCE TO RELATED PATENT APPLICATIONS

The present application claims benefit of priority to U.S. Provisional Patent Application No. 61/405,107, filed Oct. 20, 2011, which is incorporated by reference.

BACKGROUND OF THE INVENTION

The process of extracting DNA from a biological sample has many applications in biotechnology, for example, in methods of diagnosing diseases. Typically, the process of isolating and purifying DNA from a cell involves disrupting the cell membrane and removing contaminants that may interfere with the subsequent use of the isolated DNA.

Contaminants such as RNA and protein may be removed from a sample comprising DNA by enzymatic degradation. Although enzymes for the degradation of RNA or protein are known in the art and readily commercially available, reaction mixtures comprising both RNA-degrading and protein-degrading enzymes are not known and would be expected to lead to inactivation of the RNA-degrading enzyme by the protein-degrading enzyme.

BRIEF SUMMARY OF THE INVENTION

The present invention provides reagent mixtures for purifying RNA-free DNA from a sample comprising DNA, RNA, and protein. In some embodiments, the reagent mixture comprises a protease, an RNase, and a detergent, wherein the protease in the reagent mixture does not substantially inactivate the RNase when the mixture is stored for at least 24 hours at 4° C.

In some embodiments, the protease is proteinase K. In some embodiments, the protease is present at a concentration of about 0.1 mg/ml to about 10 mg/ml. In some embodiments, the concentration of the protease is about 2 mg/ml.

In some embodiments, the RNase is RNase A. In some embodiments, the RNase is present at a concentration of about 0.0016 mg/ml to about 1.0 mg/ml. In some embodiments, the concentration of the RNase is about 0.08 mg/ml.

In some embodiments, the detergent is N-lauroylsarcosine sodium salt or sodium dodecyl sulfate. In some embodiments, the detergent is present at a concentration of up to 50% (v/v). In some embodiments, the concentration of the detergent is about 1% (v/v) to about 50% (v/v). In some embodiments, the concentration of the detergent is about 3% (v/v) to about 8% (v/v).

In some embodiments, the reagent mixture further comprises a buffering agent. In some embodiments, the buffering agent is tris(hydroxymethyl)aminomethane (Tris), hydroxyethylpiperazinesulfonic acid (HEPES), or piperazinediethanesulfonic acid (PIPES). In some embodiments, the buffering agent is present at a concentration of about 2 mM to about 200 mM. In some embodiments, the concentration of the buffering agent is about 100 mM.

In some embodiments, the reagent mixture has a pH of 7.0 to 8.0. In some embodiments, the reagent mixture has a pH of about 7.4.

In some embodiments, the reagent mixture further comprises a visible dye. In some embodiments, the visible dye is bromophenol blue, xylene cyanol, bromocresol green, cresol red, or orange G. In some embodiments, the visible dye is present at a concentration of about 0.001% (v/v) to about 1.0% (v/v).

In some embodiments, the reagent mixture is stable for at least one month when stored at 4° C. In some embodiments, the reagent mixture is stable for at least six months when stored at −20° C.

In some embodiments, the reagent mixture is substantially free of cells. In some embodiments, the reagent mixture is substantially free of cell lysate. In some embodiments, the reagent mixture is sterile.

In some embodiments, the reagent mixture consists essentially of:
  proteinase K;
  RNase A;
  N-lauroylsarcosine;
  Tris;
  NaCl; and
  EDTA.

The present invention also provides methods for purifying RNA-free DNA from a sample comprising DNA, RNA, and protein. In some embodiments, the method comprises:
  contacting the sample with a reagent mixture as described herein; and
  isolating the DNA from the sample.

In some embodiments, the sample comprises cells.

The present invention also provides kits comprising a reagent mixture as described herein. In some embodiments, the protease, RNase, and detergent are all contained in the same vial.

In some embodiments, the kit further comprises a buffering agent. In some embodiments, the kit further comprises materials for purifying DNA.

The present invention also provides for storing the reagent mixture as described herein. In some embodiments, the method comprises storing the reagent mixture as described above or elsewhere herein for at least three days.

In some embodiments, the storing comprises storing the mixture for at least 14 day.

In some embodiments, the storing occurs at 5° C. or less. In some embodiments, the storing occurs at about 4° C.

In some embodiments, following the storing, further comprising contacting the reaction mixture with a sample comprising cells under conditions to allow for cell lysis and degradation of RNA from the cells by the RNase.

DEFINITIONS

"Protease" or "proteinase" interchangeably refer to an enzyme that degrades or digests proteins in a biological sample. Exemplary proteases include, but are not limited to, proteinase K and pronase.

"RNase," as used herein, refers to an enzyme that degrades or digests RNA in a biological sample. Exemplary RNases include, but are not limited to, RNase A, RNase H, RNase T1, and RNase III.

A "detergent," as used herein, refers to a reagent that disrupts or reduces the integrity of a cell membrane such that the cell's structure does not remain intact, thus allowing for the extraction of nucleic acids and/or proteins from the cell. Detergents may be ionic (i.e., anionic or cationic), non-ionic, or zwitterionic. Exemplary detergents include, but are not limited to, anionic detergents such as N-lauroylsarcosine sodium salt and sodium dodecyl sulfate.

A "buffering agent," as used herein, refers to an agent that can stabilize the pH of the reagent mixture within a specified range. Exemplary buffering agents include, but are not limited to, Tris-hydroxyaminomethane (Tris), hydroxyethylpiperazinesulfonic acid (HEPES), and piperazinediethanesulfonic acid (PIPES). Water is not considered a buffering agent for the purposes of this invention. Generally, the buffering agent will have more buffering strength than water.

"Stable" refers to the ability of an enzyme or enzymes in a reagent mixture to retain enzymatic activity. As used herein, an enzyme is said to "retain enzymatic activity" if the activity of the enzyme is at least 50%, preferably at least 60%, 70%, 80%, 90%, 95%, or more of the activity of a corresponding enzyme that has been stored under the same storage conditions (i.e., temperature) but not in a reagent mixture of the present invention. In some embodiments, the length of time that a reagent mixture is stable varies according to the conditions in which the reagent mixture is stored.

A "sample," as used herein, generally refers to cells, tissues, fluids, or other biological materials. In some embodiments, the sample is from a subject, such as a human or a non-human animal and includes, but is not limited to plasma, serum, spinal fluid, lymph fluid, the external sections of the skin, respiratory, intestinal and genitourinary tracts, tears, nasal secretions, saliva, blood cells, tumors, organs, tissue, and sample of in vitro cell culture constituents.

DETAILED DESCRIPTION OF THE INVENTION

I. Introduction

It has been found that solutions comprising protease and RNase in a single reaction mixture tolerate the presence of the protease with the RNase. These solutions have been found to be surprisingly stable over an extended storage period, and do not exhibit substantial digestion and/or inactivation of the RNase by the protease.

Accordingly, the present invention provides compositions for purifying DNA that is free of RNA contamination from a biological sample. The reagent mixture for purifying the DNA comprises a protease, an RNase, and a detergent in one solution. The present invention also provides methods for purifying DNA that is free of RNA contamination from a biological sample using a reagent mixture as described herein.

The compositions and methods of the present invention are useful, for example, for any research, diagnostic, or other biotechnological application where it is desirable to have purified RNA-free DNA.

II. Reagent Mixtures for Purifying RNA-Free DNA

In one aspect, the present invention provides reagent mixtures for purifying RNA-free DNA from a sample. This reagent mixture comprises a protease, an RNase, and a detergent.

Such reagent mixtures are useful, for example, for DNA purification protocols at least by providing three functions in one mixture:
1) membrane or cell lysis via the detergent;
2) digestion of proteins in the sample, including chromatin protein to release genomic DNA; and
3) digestion of RNA.

Thus, the reagent mixtures described herein provide a single convenient ready-to-use mixture combining different functions that had previously been provided separately. Specifically, prior to the present invention, proteases and RNases were added to samples separately to avoid digestion of the RNase by the protease. Therefore, additional containers and additional steps were required during DNA purification, resulting in clutter and possible error. Because the inventors have discovered that RNases are stable in the presence of proteases in the mixtures described herein, one can store such mixtures well before use, thereby allowing for generation, for example, of commercial kits having all cell lysis reagents in a single container.

A reagent mixture comprising a protease, an RNase, and a detergent in the same solution can be stored without the protease substantially inactivating the RNase. As used herein, "does not substantially inactivate" means that in a reagent mixture of the present invention, the enzymatic activity of the RNase is not significantly less than the enzymatic activity of a corresponding RNase that has not been stored in the same solution as the protease, i.e., that has been stored in a protease-free solution. In some embodiments, the enzymatic activity of the RNase in a reagent mixture of the present invention is at least 50%, e.g., at least 60%, 70%, 80%, 90%, 95%, or more of the enzymatic activity of a corresponding RNase that has not been stored in the same solution as a protease.

The reagent mixtures comprising protease, RNase, and detergent in the same solution can be stably stored under any condition that is suitable for preserving or retaining enzymatic activity of a protease and/or RNase. In some embodiments, the reagent mixture is stored at a temperature ranging from about −20° C. to about 25° C. In some embodiments, the reagent mixture is stored at ambient temperature and is stable for at least 3 days, at least 4 days, 5 days, 6 days, 7 days, or longer when stored at ambient temperature. In some embodiments, the reagent mixture is stored at about 4° C. and is stable for at least 30 days or one month, at least 60 days or two months, at least 90 days or three months, at least 120 days or four months, or longer when stored at about 4° C. In some embodiments, the reagent mixture is stored at about −20° C. and is stable for at least 180 days or six months, at least 210 days or seven months, at least 240 days or eight months, at least 270 days or nine months, at least 300 days or ten months, at least 365 days or one year, or longer when stored at about −20° C. One of skill in the art will recognize that fluctuations in storage conditions (i.e., storage temperature) will increase or decrease the length of time that the reagent mixture is stable.

In some embodiments, the reagent mixture of the present invention has a pH of about 7.0 to about 8.0. In some embodiments, the reagent mixture has a pH of about 7.2 to about 7.6. In some embodiments, the reagent mixture has a pH of about 7.4.

In some embodiments, the reagent mixture is substantially free of cells and/or cell lysate and/or DNA and/or RNA. In some embodiments, the reagent mixture is sterile.

In some embodiments, the reagent mixtures comprise, consist of, or consist essentially of a protease, and RNase, and a detergent. In some embodiments, the reagent mixtures comprise, consist of, or consist essentially of a protease, and RNase, a detergent, and one or more of at least one buffering agent, at least one salt, at least one chelating agent, and at least one visible dye.

A. Protease

A protease of the present invention is any enzyme that degrades proteins in a sample of interest. A wide variety of proteases can be used according to the present invention, including but not limited to serine proteases, threonine proteases, cysteine proteases, aspartate proteases, metalloproteases, and glutamic acid proteases. Proteases used can include naturally occurring proteases, recombinant proteases, and modified proteases (e.g., proteases comprising mutations, insertions, fusions, or deletions).

Exemplary proteases include, but are not limited to, proteinase K and pronase. Other exemplary proteases include proprietary commercial proteases, including but not limited to OB Protease (Omega Bio-Tek, Norcross, Ga.) and Qiagen Protease (Qiagen, Valencia, Calif.).

In some embodiments, the protease is present in the reagent mixture at a concentration of about 0.1 mg/ml to about 10 mg/ml. In some embodiments, the protease is present at a concentration of about 0.5 mg/ml to about 7 mg/ml. In some embodiments, the protease is present at a concentration of about 1 mg/ml to about 5 mg/ml. In some embodiments, the protease is present at a concentration of about 2 mg/ml.

B. RNase

An RNase of the present invention is any enzyme that degrades RNA in a sample of interest. In some embodiments, the enzyme cuts or digests RNA in a sequence non-specific manner.

Exemplary RNases include, but are not limited to, RNase H (i.e., RNase H, RNase H1, and RNase H2), RNase A, RNase T1, and RNase I. Other exemplary RNases include proprietary commercial RNases or RNase cocktails, including but not limited to RiboShredder™ (Epicentre, Madison, Wis.) and RNase Cocktail™ (Ambion, Austin, Tex.).

RNases used can include naturally occurring RNases, recombinant RNases, and modified RNases (e.g., RNases comprising mutations, insertions, or deletions). An example of a modified RNase is Hybridase™ Thermostable RNase H (Epicentre), which includes mutations that allow for greater thermostability.

In some embodiments, the RNase is present in the reagent mixture at a concentration of about 0.0016 mg/ml to about 1.0 mg/ml. In some embodiments, the RNase is present at a concentration of about 0.04 mg/ml to about 0.5 mg/ml. In some embodiments, the RNase is present at a concentration of about 0.08 mg/ml.

C. Detergent

In some embodiments, the reagent mixture of the present invention comprises a detergent. A detergent of the present invention is any reagent that disrupts the cell membrane of a cell (i.e., a surfactant).

Non-ionic detergents are an exemplary class of agents that disrupt cell membranes. Exemplary non-ionic detergents include, but are not limited to, NP40, Tween20, and Triton X-100.

Zwitterionic detergents are another exemplary class of agents that disrupt cell membranes. Exemplary zwitterionic detergents include, but are not limited to, CHAPS and sulfobetaine.

Ionic detergents are yet another exemplary class of agents that disrupt cell membranes. Exemplary ionic detergents include, but are not limited to, sodium dodecyl sulfate (SDS), sodium deoxycholate, and N-lauroylsarcosine sodium salt.

In some embodiments, the detergent is present in the reagent mixture at a concentration of up to about 50% (v/v). In some embodiments, the detergent is present at a concentration of about 1% (v/v) to about 50% (v/v). In some embodiments, the detergent is present at a concentration of about 2% (v/v) to about 20% (v/v). In some embodiments, the detergent is present at a concentration of about 2% (v/v) to about 10% (v/v). In some embodiments, the detergent is present at a concentration of about 3% (v/v) to about 8% (v/v). In some embodiments, the detergent is present at a concentration of about 5% (v/v).

D. Additional Components

Optionally, the reagent mixture comprising a protease, an RNase, and a detergent further comprises one or more components, including but not limited to, buffering agents, salts, and chelating agents.

In some embodiments, the reagent mixture further comprises a buffering agent. A buffering agent of the present invention is any agent that can stabilize the pH of the reagent mixture within a specified range. Generally, a buffering agent is an agent that has a stronger buffering capacity than water. In some embodiments, the buffering agent is a reagent that has an effective pH range between about 7.0 and about 8.0. Exemplary buffering agents are known in the art and include, but are not limited to, tris(hydroxymethyl)aminomethane (Tris), tris(hydroxymethyl)-2-aminoethanesulfonic acid (TES), hydroxyethylpiperazinesulfonic acid (HEPES), piperazinediethanesulfonic acid (PIPES), 4-morpholinepropanesulfonic acid (MOPS), N,N-Bis(2-hydroxyethyl)-3-amino-2-hydroxypropanesulfonic acid (DISPO), and N-[Tris (hydroxymethyl)methyl]-3-amino-2-hydroxypropanesulfonic acid (TAPSO). In some embodiments, the buffering agent is present in the reaction mixture at a concentration of about 2 mM to about 200 mM. In some embodiments, the buffering agent is present at a concentration of about 20 mM to about 180 mM. In some embodiments, the buffering agent is present at a concentration of about 50 mM to about 150 mM. In some embodiments, the buffering agent is present at a concentration of about 100 mM.

In some embodiments, the reagent mixture further comprises a salt. Exemplary salts include, but are not limited to, sodium chloride and potassium chloride. In some embodiment, the salt is present in the reagent mixture at a concentration of about 5 mM to about 500 mM. In some embodiments, the salt is present at a concentration of about 25 mM to about 200 mM. In some embodiments, the salt is present at a concentration of about 50 mM to about 150 mM. In some embodiments, the salt is present at a concentration of about 100 mM.

In some embodiments, the reagent mixture further comprises a chelating agent. Examples of suitable chelating agents include, but are not limited to, ethylenediamine tetraacetic acid (EDTA), ethyleneglycol tetraacetic acid (EGTA), bis(2-aminophenoxy)ethane tetraacetic acid (BAPTA), and citric acid. In some embodiments, the chelating agent is present in the reagent mixture at a concentration of about 2 mM to about 200 mM. In some embodiments, the chelating agent is present at a concentration of about 20 mM to about 180 mM. In some embodiments, the chelating agent is present at a concentration of about 50 mM to about 150 mM. In some embodiments, the chelating agent is present at a concentration of about 100 mM.

In some embodiments, the reagent mixture further comprises one or more visible dyes for use in visually tracking the addition of the reaction mixture to the samples. Examples of suitable visible dyes include, but are not limited to, bromophenol blue, xylene cyanol, bromocresol green, cresol red, and orange G. In some embodiments, the visible dye is present at a concentration of about 0.001% (v/v) to about 1.0% (v/v). In some embodiments, the visible dye is present at a concentration of about 0.005% (v/v) to about 0.5% (v/v). In some embodiments, the visible dye is present at a concentration of about 0.01% (v/v) to about 0.1% (v/v).

Exemplary reagent mixtures include, but are not limited to:
proteinase K at a concentration of about 1 mg/ml to about 5 mg/ml (e.g., 1, 2, 3, 4, or 5 mg/ml), RNase A at a concentration of about 0.04 mg/ml to about 0.5 mg/ml (e.g., 0.04, 0.08, 0.12, 0.16, 0.2, 0.25, 0.3, 0.35, 0.4, 0.45, or 0.5 mg/ml), N-lauroylsarcosine sodium salt at a concentration of about 3% (v/v) to about 8% (v/v) (e.g., 3, 4, 5, 6, 7, or 8% (v/v)), Tris at a pH of about 7.0 to about 8.0 (e.g., pH 7.0, 7.1, 7.2, 7.3, 7.4, 7.5, 7.6, 7.7, 7.8, 7.9, or 8.0) and at a concentration of about 50 mM to about 150 mM (e.g., 50, 60, 70, 80, 90, 100, 110, 120, 130, 140, or 150 mM), potassium chloride at a concentration of about 50 mM to about 150 mM (e.g., 50, 60, 70, 80, 90, 100, 110, 120, 130, 140, or 150 mM), and EDTA at a concentration of about 50 mM to about 150 mM (e.g., 50, 60, 70, 80, 90, 100, 110, 120, 130, 140, or 150 mM);

proteinase K at a concentration of about 1 mg/ml to about 5 mg/ml (e.g., 1, 2, 3, 4, or 5 mg/ml), RNase A at a concentration of about 0.04 mg/ml to about 0.5 mg/ml (e.g., 0.04, 0.08, 0.12, 0.16, 0.2, 0.25, 0.3, 0.35, 0.4, 0.45, or 0.5 mg/ml), N-lauroylsarcosine sodium salt at a concentration of about 3% (v/v) to about 8% (v/v) (e.g., 3, 4, 5, 6, 7, or 8% (v/v)), HEPES at a pH of about 7.0 to about 8.0 (e.g., pH 7.0, 7.1, 7.2, 7.3, 7.4, 7.5, 7.6, 7.7, 7.8, 7.9, or 8.0) and at a concentration of about 50 mM to about 150 mM (e.g., 50, 60, 70, 80, 90, 100, 110, 120, 130, 140, or 150 mM), potassium chloride at a concentration of about 50 mM to about 150 mM (e.g., 50, 60, 70, 80, 90, 100, 110, 120, 130, 140, or 150 mM), and EDTA at a concentration of about 50 mM to about 150 mM (e.g., 50, 60, 70, 80, 90, 100, 110, 120, 130, 140, or 150 mM);

proteinase K at a concentration of about 1 mg/ml to about 5 mg/ml (e.g., 1, 2, 3, 4, or 5 mg/ml), RNase A at a concentration of about 0.04 mg/ml to about 0.5 mg/ml (e.g., 0.04, 0.08, 0.12, 0.16, 0.2, 0.25, 0.3, 0.35, 0.4, 0.45, or 0.5 mg/ml), sodium dodecyl sulfate at a concentration of about 3% (v/v) to about 8% (v/v) (e.g., 3, 4, 5, 6, 7, or 8% (v/v)), Tris at a pH of about 7.0 to about 8.0 (e.g., pH 7.0, 7.1, 7.2, 7.3, 7.4, 7.5, 7.6, 7.7, 7.8, 7.9, or 8.0) and at a concentration of about 50 mM to about 150 mM (e.g., 50, 60, 70, 80, 90, 100, 110, 120, 130, 140, or 150 mM), sodium chloride at a concentration of about 50 mM to about 150 mM (e.g., 50, 60, 70, 80, 90, 100, 110, 120, 130, 140, or 150 mM), and EDTA at a concentration of about 50 mM to about 150 mM (e.g., 50, 60, 70, 80, 90, 100, 110, 120, 130, 140, or 150 mM);

proteinase K at a concentration of about 1 mg/ml to about 5 mg/ml (e.g., 1, 2, 3, 4, or 5 mg/ml), RNase A at a concentration of about 0.04 mg/ml to about 0.5 mg/ml (e.g., 0.04, 0.08, 0.12, 0.16, 0.2, 0.25, 0.3, 0.35, 0.4, 0.45, or 0.5 mg/ml), N-lauroylsarcosine sodium salt at a concentration of about 3% (v/v) to about 8% (v/v) (e.g., 3, 4, 5, 6, 7, or 8% (v/v)), Tris at a pH of about 7.0 to about 8.0 (e.g., pH 7.0, 7.1, 7.2, 7.3, 7.4, 7.5, 7.6, 7.7, 7.8, 7.9, or 8.0) and at a concentration of about 50 mM to about 150 mM (e.g., 50, 60, 70, 80, 90, 100, 110, 120, 130, 140, or 150 mM), sodium chloride at a concentration of about 50 mM to about 150 mM (e.g., 50, 60, 70, 80, 90, 100, 110, 120, 130, 140, or 150 mM); and EDTA at a concentration of about 50 mM to about 150 mM (e.g., 50, 60, 70, 80, 90, 100, 110, 120, 130, 140, or 150 mM);

proteinase K at a concentration of about 1 mg/ml to about 5 mg/ml (e.g., 1, 2, 3, 4, or 5 mg/ml), RNase A at a concentration of about 0.04 mg/ml to about 0.5 mg/ml (e.g., 0.04, 0.08, 0.12, 0.16, 0.2, 0.25, 0.3, 0.35, 0.4, 0.45, or 0.5 mg/ml), sodium dodecyl sulfate at a concentration of about 3% (v/v) to about 8% (v/v) (e.g., 3, 4, 5, 6, 7, or 8% (v/v)), HEPES at a pH of about 7.0 to about 8.0 (e.g., pH 7.0, 7.1, 7.2, 7.3, 7.4, 7.5, 7.6, 7.7, 7.8, 7.9, or 8.0) and at a concentration of about 50 mM to about 150 mM (e.g., 50, 60, 70, 80, 90, 100, 110, 120, 130, 140, or 150 mM), sodium chloride at a concentration of about 50 mM to about 150 mM (e.g., 50, 60, 70, 80, 90, 100, 110, 120, 130, 140, or 150 mM), and EDTA at a concentration of about 50 mM to about 150 mM (e.g., 50, 60, 70, 80, 90, 100, 110, 120, 130, 140, or 150 mM); and proteinase K at a concentration of about 1 mg/ml to about 5 mg/ml (e.g., 1, 2, 3, 5 mg/ml), RNase A at a concentration of about 0.04 mg/ml to about 0.5 mg/ml (e.g., 0.04, 0.08, 0.12, 0.16, 0.2, 0.25, 0.3, 0.35, 0.4, 0.45, or 0.5 mg/ml), sodium dodecyl sulfate at a concentration of about 3% (v/v) to about 8% (v/v) (e.g., 3, 4, 5, 6, 7, or 8% (v/v)), Tris at a pH of about 7.0 to about 8.0 (e.g., pH 7.0, 7.1, 7.2, 7.3, 7.4, 7.5, 7.6, 7.7, 7.8, 7.9, or 8.0) and at a concentration of about 50 mM to about 150 mM (e.g., 50, 60, 70, 80, 90, 100, 110, 120, 130, 140, or 150 mM), potassium chloride at a concentration of about 50 mM to about 150 mM (e.g., 50, 60, 70, 80, 90, 100, 110, 120, 130, 140, or 150 mM), and EDTA at a concentration of about 50 mM to about 150 mM (e.g., 50, 60, 70, 80, 90, 100, 110, 120, 130, 140, or 150 mM).

III. DNA Purification Methods

The present invention provides methods of purifying DNA that is free of RNA contamination from a sample comprising DNA, RNA, and protein by contacting the sample with the reagent mixture comprising a protease, an RNase, and a detergent as described herein.

The methods of the present invention can be performed on any sample containing DNA, including but not limited to, cells, tissue biopsies (e.g., solid tumors or tissues suspect of having cancer or pre-cancerous tissue), blood samples, stool samples, etc.

In some embodiments, the sample comprises cells. A variety of prokaryotic and eukaryotic cells can be used in the present invention. In some embodiments, the cells are animal cells, including but not limited to, human, or non-human, mammalian cells. Non-human mammalian cells include but are not limited to, primate cells, mouse cells, rat cells, porcine cells, and bovine cells. In some embodiments, the cells are plant or fungal (including but not limited to yeast) cells. Cells can be, for example, cultured primary cells, immortalized culture cells or can be from a biopsy or tissue sample, optionally cultured and stimulated to divide before assayed. Cultured cells can be in suspension or adherent prior to and/or during the permeabilization and/or DNA modification steps. Cells can be from animal tissues, biopsies, etc. For example, the cells can be from a tumor biopsy.

The quantity of reagent mixture used, as well as the length of time that the reagent mixture is contacted to the sample, will depend on the components that comprise the reagent mixture and the concentration of each component in the reagent mixture. Those of skill in the art will appreciate how to adjust conditions depending on the composition of the reagent mixture. Generally, the conditions of the reagent mixture-sample incubation step are adjusted such that the isolated DNA is substantially free of RNA. "Substantially free," as used herein, means that the DNA that is isolated comprises less than 10% RNA, e.g., less than 5%, 4%, 3%, 2%, 1% or less. The level of purity that is required for isolated DNA (i.e., the extent to which the DNA is substantially free of RNA) may vary depend on the intended downstream use of the isolated DNA. Purity and homogeneity are typically determined using molecular biology techniques such as agarose gel electrophoresis or measuring optical density (UV absorbance). Those of skill in the art will recognize that the quality of the sample may inhibit the degradation of RNA and protein contaminants and the extent to which DNA can be made substantially free of RNA.

Following the digestion of protein and RNA in the sample, genomic DNA is isolated from the sample according to any method known in the art. In some embodiments, phenol/chloroform extractions are used and the DNA can be subsequently precipitated (e.g., by ethanol) and purified. Alternatively, DNA can be isolated on a nucleic-acid binding column.

IV. Kits

The present invention also provides kits for performing the DNA purification methods of the claimed invention. A kit can optionally include written instructions or electronic instructions (e.g., on a CD-ROM or DVD). Kits of the present invention can include a reagent mixture comprising in the same vial or container a protease, an RNase, and a detergent. The proteases, RNases, and detergents can include those described herein in detail. In some embodiments, the protease is proteinase K; the RNase is RNase A, RNase H, or RNase T1; and the detergent is N-lauroylsarcosine sodium salt or sodium dodecyl sulfate. In some embodiments, the kits further comprise a buffering agent, a salt, a chelating agent, and/or a visible dye. The buffering agents, salts, chelating agents, and visible dyes can include those described herein in detail. In some embodiments, the buffering agents, salts, chelating agents, and/or visible dyes are included in the same reagent mixture that comprises the protease, RNase, and detergent.

The kits of the invention can also include materials for the further isolation of DNA. Such materials include, but are not limited to, spin columns, wash buffers, elution buffers, and collection tubes. In some embodiments, the kits comprise a chaotropic agent that promotes the binding of the DNA to the isolation column. Examples of suitable chaotropic agents include, but are not limited to, guanidine hydrochloride.

In some embodiments, the kits of the invention comprise one or more of the following:
(i) a reagent mixture comprising a protease, an RNase, and a detergent, and optionally a buffering agent, salt, chelating agent, and/or visible dye;
(ii) a chaotropic agent;
(iii) materials (reagents and/or consumables) for the isolation of nucleic acids (e.g., spin columns).

EXAMPLES

The following example is offered to illustrate, but not to limit the claimed invention.

Described herein is a procedure for the isolation and analysis of DNA that is free of RNA contamination from an adherent cell line grown in culture using a reagent mixture as described herein.

For cultured cells in a multi-well plate, media is aspirated from the cultured cells. The cells are rinsed with 1 ml of phosphate-buffered saline (PBS) and the PBS is aspirated. 200 µl of PBS is added to each well and swirled gently. 50 µl of reagent mixture, comprising Tris pH 7.4, NaCl, EDTA, N-Lauroylsarcosine sodium salt, Proteinase K, and RNase A, is then added to each well and swirled to lyse the cells. The cells are incubated with the reagent mixture at 37° C. for 10 minutes. Following incubation, 250 µl of a 4 M guanidine solution is added to the cells, then 250 µl of 100% ethanol is added to the cells and the mixture is mixed well. Genomic DNA is then purified using any standard, column-based DNA or RNA isolation kit. The isolated nucleic acid is then analyzed by gel electrophoresis and is found to contain only genomic DNA, with no RNA being detected.

Functional analysis of the reagent mixture as described above stored at different temperatures demonstrated that the reagent mixture was stable for two weeks if stored at 15° C. If the reagent mixture was stored at room temperature (23° C.) it was stable for 60 hours. Accelerated stability studies of the described reagent mixture indicated that the reagent mixture was stable for greater than 2 years at −20° C. Additionally, real-time stability data indicated that the reagent mixture was stable for at least 9 months at −20° C.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A reagent mixture for purifying RNA-free DNA from a sample comprising DNA, RNA, and protein, the reagent mixture comprising:
   a protease, wherein the protease is present at a concentration of 0.5 mg/ml to about 7 mg/ml;
   an RNase;
   a detergent, and
   a buffering agent;
   wherein the reagent mixture is substantially free of cells or cell lysate and wherein the protease in the reagent mixture does not substantially inactivate the RNase when the mixture is stored for at least 24 hours at 4° C.

2. The reagent mixture of claim 1, wherein the protease is proteinase K.

3. The reagent mixture of claim 1, wherein the protease is present at a concentration of about 1 mg/ml to about 5 mg/ml.

4. The reagent mixture of claim 1, wherein the RNase is RNase A.

5. The reagent mixture of claim 1, wherein the RNase is present at a concentration of about 0.0016 mg/ml to about 1.0 mg/ml.

6. The reagent mixture of claim 1, wherein the detergent is N-lauroylsarcosine sodium salt or sodium dodecyl sulfate.

7. The reagent mixture of claim 1, wherein the detergent is present at a concentration of up to 50% (v/v).

8. The reagent mixture of claim 1, wherein the buffering agent has an effective pH range between about 7.0 and about 8.0.

9. The reagent mixture of claim 1, wherein the buffering agent is tris(hydroxymethyl)aminomethane (Tris), hydroxyethylpiperazinesulfonic acid (HEPES), or piperazinediethanesulfonic acid (PIPES).

10. The reagent mixture of claim 1, wherein the buffering agent is present at a concentration of about 2 mM to about 200 mM.

11. The reagent mixture of claim 1, further comprising a visible dye.

12. The reagent mixture of claim 11, wherein the visible dye is bromophenol blue, xylene cyanol, bromocresol green, cresol red, or orange G.

13. The reagent mixture of claim 11, wherein the visible dye is present at a concentration of about 0.001% (v/v) to about 1.0% (v/v).

14. The reagent mixture of claim 1, wherein the mixture is stable for at least one month when stored at 4° C.

15. The reagent mixture of claim 1, wherein the reagent mixture is sterile.

16. The reagent mixture of claim 1, consisting essentially of:
proteinase K;
RNase A;
N-lauroylsarcosine;
Tris;
NaCl; and
EDTA.

17. The reagent mixture of claim 1, further comprising one or more of at least one salt and at least one chelating agent.

18. The reagent mixture of claim 1, comprising:
proteinase K at a concentration of about 1 mg/ml to about 5 mg/ml;
RNase A at a concentration of about 0.04 mg/ml to about 0.5 mg/ml;
N-lauroylsarcosine sodium salt or sodium dodecyl sulfate at a concentration of about 3% (v/v) to about 8% (v/v); and
tris(hydroxymethyl)aminomethane (Iris) or hydroxyethylpiperazinesulfonic acid (HEPES) at a concentration of about 50 mM to about 150 mM.

19. The reagent mixture of claim 18, further comprising one or more of:
potassium chloride or sodium chloride at a concentration of about 50 in M to about 150 mM; and
ethylenediamine tetraacetic acid (EDTA) at a concentration of about 50 mM to about 150 mM.

20. A kit comprising the reagent mixture of claim 1, wherein the protease, RNase, and detergent are all contained in the same vial.

21. A method for purifying RNA-free DNA from a sample comprising DNA, RNA, and protein, the method comprising:
contacting the sample with a reagent mixture of claim 1; and
isolating the DNA from the sample.

22. A method of storing the reagent mixture of claim 1, comprises storing the reagent mixture for at least three days.

* * * * *